US00PP10968P

United States Patent [19]

Bak et al.

[11] Patent Number: Plant 10,968

[45] Date of Patent: Jun. 22, 1999

[54] GUZMANIA PLANT NAMED 'JIVE'

[75] Inventors: Elly Bak, Rijsenhout; Nicolaas D. M. Steur, Oude Niedorp, both of Netherlands

[73] Assignee: Corn. Bak B.V., AA Assendelft, Netherlands

[21] Appl. No.: 08/993,463

[22] Filed: Dec. 18, 1997

[51] Int. Cl.[6] ..... A01H 5/00

[52] U.S. Cl. ..... Plt./371

[58] Field of Search ..... Plt./88.8

*Primary Examiner*—Elizabeth Kemmerer

*Attorney, Agent, or Firm*—Foley & Lardner

[57] ABSTRACT

A new cultivar of Guzmania plant named 'Jive' characterized by the combined features of a plant form that is funnel-form rosette; plant height of approximately 47 cm; linear-lanceolate leaves measuring 28–37 cm in length and 3.5–4 cm in width; leaf color upperside of R.H.S. 146A and underside of R.H.S. 147B; primary bract color of R.H.S. 169A; and top primary bract color of R.H.S. 23A.

1 Drawing Sheet

The present invention comprises a new and distinct cultivar of Guzmania that is an cross-hybrid, within the genus of Guzmania of the family *bromeliaceae.*

BACKGROUND OF THE INVENTION

Guzmania are predominantly epiphytic with a few terrestrial species and are native to the tropics. For the most part species vary in diameter from 7 or 8 inches to 3 or 4 feet and have rosettes of glossy, smooth edged leaves.

Floral bracts of Guzmania frequently have brilliant colors and may last for many months. The range of colors for Guzmania is generally from yellow through orange but may also include flame red and red-purple. White or yellow, tubular, three petalled flowers may also appear on a stem or within the leaf rosette but are usually short lived.

Guzmania may be advantageously grown as pot plants for greenhouse or home use. The plants are generally grown in shade and during the spring to autumn period the central vase-like part of the leaf rosette is filled with water.

Guzmania is native to tropical America. Leaves of Guzmania are usually formed as basal rosettes which are stiff and entire and in several vertical ranks. Guzmania have terminal spikes or panicles which are often bracted with petals united in a tube about as long as the calyx. The ovary is superior and the seeds plumose.

Asexual propagation of Guzmania is frequently done through the use of tissue culture practices. Propagation can also be from off-shoots produced by the plant which may then be rooted. The resulting plantlets are detached from the mother plant and may be potted up in a suitable growing mixture.

Methods for cultivation and breeding of Guzmania are well known. For a detailed discussion, reference is made to the following publications, which are incorporated herein by reference. Benzing, David H., *The Biology of the Bromeliads,* Mad River Press, Inc., Eureka (1980); Zimmer, Karl, *Bromelien,* Verlag Paul Parey, Berlin (1986); and Rauh, Werner, *Bromelien,* Verlag Eugen Ulmer, Stuttgart (1981).

The new cultivar 'Jive' is a product of a planned breeding program and was originated by the inventors from a cross made during such a program in Assendelft, The Netherlands, in 1987. The male or pollen parent was a selection of a mutation of *Guzmania wittmackii,* identified by Code No. 8706860. The female or seed parent was a selection of *Guzmania lingulata,* identified by Code No. 8705809.

The selection comprising the new variety was chosen from among the progeny of the above cross following commencement of flowering in 1989 in Assendelft, The Netherlands. The selection was first asexually propagated through off-shoots by, or under the supervision of, the inventors in Assendelft, with subsequent asexual reproduction through tissue culture in 1990. The first plants propagated through the use of a tissue-culture flowered in 1996. Continuous asexual propagation has demonstrated that the combination of characteristics as herein disclosed for the new cultivar 'Jive', as observed in Assendelft, the Netherlands, are firmly fixed and are retained through successive generations of asexual reproduction.

'Jive' has not been tested under all available environmental conditions. The phenotype may vary with variations in environmental conditions such as temperature, light intensity, frequency of fertilization, composition of fertilizer, acetylene treatment, day length and humidity without, however, any change in the genotype of the new cultivar.

The closest comparison cultivar is Guzmania 'Rumba' described in copending application Ser. No. 08/813,179 now Plant Patent 10,575. The most important difference between these cultivars is that 'Jive' has a more compact growth habit than 'Rumba'.

BRIEF SUMMARY OF THE INVENTION

'Jive' is particularly characterized by the following characteristics:

1. Plant form that is a funnel-shaped rosette;

2. Plant height of approximately 47 cm;

3. Linear lanceolate leaves measuring 28–37 cm in length and 3.5–4 cm in width;

4. Leaf color upperside of R.H.S. 146A and underside of R.H.S. 147B;

5. Primary bract color of R.H.S. 169A; and

6. Top primary bract color of R.H.S. 23A.

Guzmania 'Jive' is a solid, long-lasting hybrid with superior bract-production and a compound and orange inflorescence that exhibits good keeping quality.

BRIEF DESCRIPTION OF THE DRAWINGS

The accompanying color photographs show typical inflorescence and foliage characteristics of 'Jive', with the colors being as true as possible with illustrations of this type. Phenotypic expressions may vary with differences in growth, environmental and cultural conditions:

Sheet 1 is a side view of a specimen of 'Jive' showing the primary and floral bracts.

DETAILED BOTANICAL DESCRIPTION

The following traits have been repeatedly observed and in combination distinguish 'Jive' as a new and distinct cultivar. These observations, measurements and descriptions were taken for 'Jive' plants grown under greenhouse conditions which approximate those generally used in commercial practice. The new cultivar flowers approximately 14 weeks after treatment with acetylene.

Classification:
*Botanical.*—*Guzmania wittmackii*×*lingulata,* cv. 'Jive'.

FLOWERS

Borne (stalks): Erect.
Shape: Compound.
Size of infloresence on stalk: Approximately 13 cm high.
Diameter infloresence: Approximately 21 cm.
Individual petals: mostly within the floral bracts hidden behind the primary bracts.
*Length.*—Approximately 6 cm.
*Width.*—Approximately 0.5 cm.
*Quantity.*—Approximately 70 flowers divide over approximately 10 branches depending on the size of the plant.
*Color.*—R.H.S. 17A.
*Time of blooming.*—A fully grown plant can bloom the whole year starting±14 weeks after induction naturel or through treatment with acetylene.
*Duration of blooming.*—Each flower blooms 1 day and the total of blooming can be about 6 weeks.
Reproductive organs:
*Ovaries.*—Superior.
*Stamens.*—6 in number.
*Seed characteristics.*—Sterile hybrid therefore no fruit or seed.

PLANT

General appearance:
*Form.*—Funnel form rosette.
*Height.*—Approximately 47 cm high (flowering).
*Growth habit.*—Stemless.
*Diameter.*—Approximately 55 cm.

FOLIAGE

Color (changes dependent on environmental conditions):
*Upper surface.*—R.H.S. 146A.
*Under surface.*—R.H.S. 147B.
Size of leaf:
*Length.*—Approximately 28–37 cm.
*Width.*—Approximately 3.5–4.0 cm.
Shape: Linear-lanceolate.
Surface texture: Smooth.

BRACTS

Length:
*Scape bracts.*—The lowest approximately 32 cm and approximately 16 cm just below the primary bracts.
*Primary bracts.*—The lowest approximately 16 cm and approximately 7 cm at the top.
Width:
*Scape bracts.*—Approximately 3.5–4.0 cm.
*Primary bracts.*—Approximately 3.0–3.5 cm.
Number:
*Scape bracts.*—Approximately 10.
*Primary bracts.*—Approximately 14.
General shape: Lanceolate.
Texture: Smooth.
Margin: Entire.
Color:
*Primary bracts.*—R.H.S. 169A.
*Top primary bracts.*—R.H.S. 23A.

We claim:

1. A new and distinct cultivar of Guzmania plant named 'Jive', as illustrated and described.

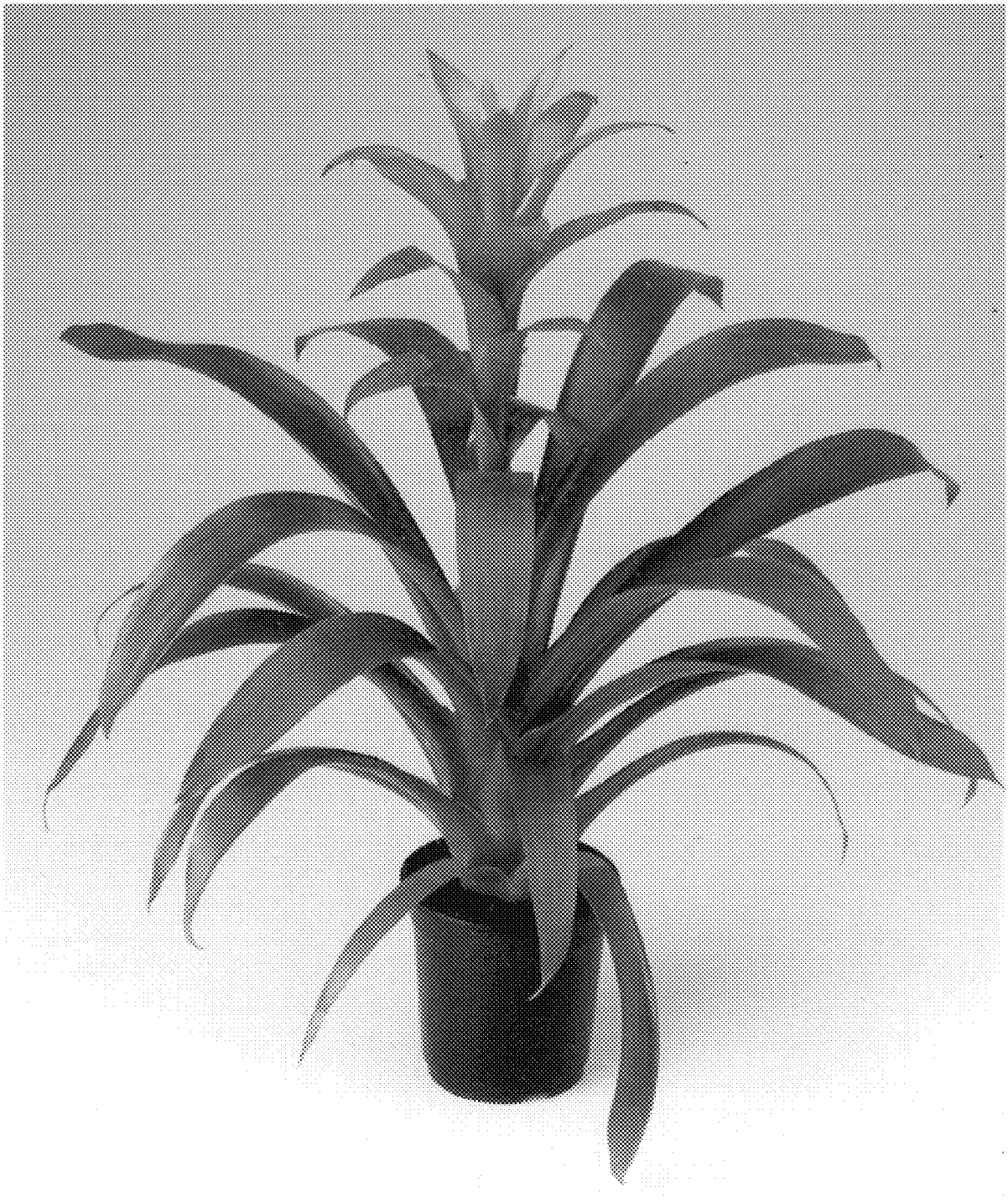

* * * * *